United States Patent
Zhou et al.

(10) Patent No.: US 11,261,373 B2
(45) Date of Patent: Mar. 1, 2022

(54) PREPARATION METHOD OF SUPERCRITICAL CARBON DIOXIDE THICKENER FOR TIGHT OIL AND GAS RESERVOIR

(71) Applicant: Southwest Petroleum University, Sichuan (CN)

(72) Inventors: Ming Zhou, Sichuan (CN); Hongjun Tu, Sichuan (CN); Xiao Guo, Sichuan (CN); Jinfeng Zhang, Sichuan (CN); Juncheng Bu, Sichuan (CN); Peng'ao Peng, Sichuan (CN); Hongchang Han, Sichuan (CN); Linkai Li, Tianjin (CN); Mao Liao, Sichuan (CN); Yinhua Gu, Sichuan (CN); Rongjun Yi, Sichuan (CN); Yongqiang Shi, Henan (CN); Liangliang Xia, Henan (CN)

(73) Assignee: Southwest Petroleum University, Sichuan (CN)

( * ) Notice: Subject to any disclaimer, the term of this patent is extended or adjusted under 35 U.S.C. 154(b) by 0 days.

(21) Appl. No.: 16/928,567

(22) Filed: Jul. 14, 2020

(65) Prior Publication Data
US 2020/0385631 A1 Dec. 10, 2020

Related U.S. Application Data

(63) Continuation of application No. PCT/CN2019/130305, filed on Dec. 31, 2019.

(51) Int. Cl.
*C09K 8/70* (2006.01)
*C07C 273/18* (2006.01)

(52) U.S. Cl.
CPC .......... *C09K 8/70* (2013.01); *C07C 273/1836* (2013.01)

(58) Field of Classification Search
CPC .. C09K 8/70; C09K 8/62; C09K 8/594; C07C 273/1836; C07C 269/06; C07C 303/28; Y02P 20/54
See application file for complete search history.

(56) References Cited

FOREIGN PATENT DOCUMENTS

| CN | 107043620 | * | 8/2017 |
| CN | 107253922 | * | 10/2017 |
| WO | WO 00/35998 | * | 6/2000 |

* cited by examiner

*Primary Examiner* — Kumar R Bhushan

(57) ABSTRACT

The present invention disclosed a method for preparing a thickener for tight oil and gas reservoir, which relieves damages. The technical solution includes the following steps: putting a three-flask in ice; adding perfluoroalkyl alcohol, P-toluenesulfonyl chloride and pyridine; reacting for 3 h at 0-20° C.; adding filter paper; ultrasonic dispersing for 1 h; removing the filter paper; washing the solution for 3-5 times by adding dilute hydrochloric acid to collect the intermediate product (I); adding 1,3-dihydroxy-propane-2-tert-butyl carbamate and the intermediate product (I) in another three-flask; adding potassium carbonate and N,N-dimethylformamide; reacting for 4 h at 40° C. to collect the intermediate product (II); adding trifluoroacetic acid and methylene chloride into the intermediate product (II); reacting at 45° C. for 2 h; extracting and vacuum drying; and adding 1,6-hexamethylene diisocyanate; reacting for 2 h to collect the final product (III).

1 Claim, No Drawings

PREPARATION METHOD OF SUPERCRITICAL CARBON DIOXIDE THICKENER FOR TIGHT OIL AND GAS RESERVOIR

CROSS REFERENCE OF RELATED APPLICATION

This is a Continuation Application of the International Application PCT/CN2019/130305, filed Dec. 31, 2019, which claims priority under 35 U.S.C. 119(a-d) to CN 201910737149.0, filed Aug. 11, 2019.

BACKGROUND OF THE PRESENT INVENTION

Field of Invention

The present invention relates to a well stimulation technique in which rock is fractured by a fracking fluid without water for tight oil and gas reservoir to improve recovery efficiency, and more particularly to a preparation method of supercritical carbon dioxide thickener for tight oil and gas reservoir. The present invention is in the oilfield chemical field.

Description of Related Arts

The tight oil and gas reservoirs are characterized in poor physical properties, low-porosity and low-permeability, which is strongly sensitive to water. Research shows that the clay mineral in the reservoir, especially the expansive clay, and other authigenic sedimentary minerals are formation water with different mineralization. The minerals expand, disperse, fall off and migrate from the original place to cause pores to become smaller or cracks to close because the formation water with low mineralization enters the oil and gas reservoir. More small micro-pores and capillaries are formed and can absorb more and more water, which leads to severe water-sensitive damage.

The small radius of pore throat, high pressure inside the capillaries, low permeability, and strong heterogeneity lead to serious water-lock damage. The water-lock effect refers to the phenomena of reduction of gas-phase permeability due to increase in gas phase flow resistance caused by increasing water saturation from initial water saturation or irreducible water saturation to 100% water saturation after liquid phase work fluid invades the gas reservoir during the process of drilling, well completion and fracturing. The water-lock effect is essentially caused by the capillary force in the fracture. The capillary force equals the difference between the nonwetting phase pressure and the wetting phase pressure on two sides of the meniscus of capillary, which can be calculated by Laplace's Equation in an arbitrary curved surface.

Because in low permeability or tight gas reservoir, the pore throat size is small for free flow of the fluid; the gas flow channel is narrow; the seepage resistance is large; and the interaction force between liquid-solid interface and liquid-gas interface is large, too, the water lock effect become particularly prominent. Once the water lock occurs, the permeability damage rate can reach more than 70%, and the gas well production will be reduced to less than ⅓ of the original.

The broken fluid is not able to flow back in time after the water-base fracturing carry out in a tight oil and gas reservoir. Water is easily absorbed into formation to induce a serious water-sensitive damage. The water-lock effect is serious due to the small-sized pore throat, strong capillary force, which leads to low productivity or even no productivity.

An effective way to develop tight oil and gas reservoir is reservoir stimulation and to improve recovery efficiency at a later stage. The conventional technology easily induces water-lock to decrease permeability, which damages the formation, thus the anhydrous fracturing is gaining more and more attention at presents because no water is needed during the fracturing. The research on the anhydrous fracturing has significant economic and social benefits. Both Chinese patent ZL201710416147.2 (a preparation method of liquid carbon dioxide thickener) and Chinese patent ZL201710480823.2 (a preparation method of supercritical carbon dioxide thickener) can be applied in fracturing fluid and oil-displacement agent for improve recovery efficiency for tight oil and gas reservoir. The two prepared thickeners contain ester groups which can be used under low temperature and water-free environment, but they become unstable and are easily hydrolyzed in the high-temperature oil and gas reservoir with active edge or bottom waters, which lead to the gradual decrease or even disappearance of thickening capacity. The present invention prepares a four-armed oligomeric $CO_2$ thickener containing ether which improves the viscosity of the supercritical carbon dioxide and the stability in heat and water.

SUMMARY OF THE PRESENT INVENTION

An object of the present invention is to provide a preparation method of supercritical carbon dioxide thickener for tight oil and gas reservoir to avoid the damages to the reservoir by adopting the conventional exploring method.

The present invention provides the preparation method of supercritical carbon dioxide thickener for tight oil and gas reservoir, which comprises the following steps of:

(1) Preparing P-toluene perfluoroalkyl ethylenesulfonates (TFES), which further comprises following sub-steps: after adding a perfluoroalkyl alcohol and a P-toluenesulfonyl chloride in a three-neck flask, wherein a molar ratio of the perfluoroalkyl alcohol and the P-toluenesulfonyl chloride is 1:1.1-1.2, and adding a pyridine; wherein the system has reacted for 3 h under stirring thoroughly; maintaining a temperature at 0-20° C.; adding filter paper and carrying out ultrasonic dispersion for 1 h after the reaction is over, after removing unreacted residue P-toluenesulfonyl chloride and the filter paper; washing the system with 15% dilute hydrochloric acid many times to remove the pyridine and collect a white solid; washing the solid with distilled water for multiple times, drying the solid by vacuum drying oven at 40° C. for 3 h to prepare an intermediate product (I) TFES as shown in below (a);

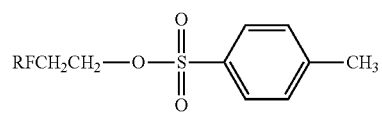

(a) Intermediate product (I) TFES (RF is one perfluoro alkyl from these groups of $C_5F_{11}$, $C_6F_{13}$, $C_7F_{15}$, $C_8F_{17}$, $CF_9F_{19}$, $C_{10}F_{21}$)

(2) Preparing intermediate product (II) (1,3-bis(perfluoroalkyl ethoxy) isopropyl-2-tertbutyl carbamate) (PFEIT), which further comprises the following sub-steps: adding the 1,3-dihydroxy-propane-2-tert-butyl carbamate and intermediate product (I) TFES in a three-neck flask, wherein a molar ratio of the 1,3-dihydroxy-propane-2-tert-butyl carbamate and TFES is 2.1-2.2:1; then adding potassium carbonate and N,N-dimethylformamide; wherein the system has been reacted for 4 h under stirring thoroughly at 40° C.; washing the reaction liquid with distilled water repeatedly after a reaction process is over; then carrying out the vacuum drying to collect an intermediate product (II) PFEIT, as shown in below (b);

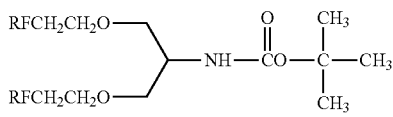

(b) Intermediate product (II) PFEIT (RF is one perfluoro alkyl from these groups of $C_5F_{11}$, $C_6F_{13}$, $C_7F_{15}$, $C_8CF_{17}$, $C_9F_{19}$, $C_{10}F_{21}$);

(3) Preparing a final product (III) 1,6-bis[1,3-bis(perfluoroalkyl ethoxy) isopropyl-2-urea]hexane (PFEIUH), which further comprises the following sub-steps: adding a mixture of methylene chloride and trifluoroacetic acid in a three-neck flask, a volume ratio of the methylene chloride and the three trifluoroacetic acid is 2:1; adding the intermediate product (III) PFEIT to the mixture; maintaining a temperature at 45°; reacting for 2 h; adding the methylene chloride for extracting for 3 times to form an organic layer; drying the organic layer with a $Na_2SO_4$; adding 1,6-hexamethylene diisocyanate (HMDI), wherein a molar ratio of HMDI and PFEIT is 1:2.05-2.10, reacting under a temperature of 50° C. for 2 h, washing a crude product with a mixture of ethyl acetate and benzene for multiple times; filtering and carrying out vacuum drying to collect a final product (III) PFEIUH as shown in below (c).

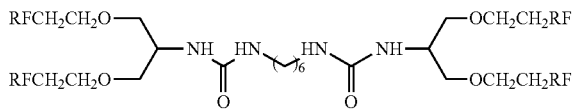

(c) Final product (III) PFEIUH (RF is one perfluoro alkyl from these of $C_5F_{11}$, $C_6F_{13}$, $C_7F_{15}$, $C_9F_{17}$, $C_9F_{19}$, $C_{10}F_{21}$)

The benefits of the present invention are as follow: the pressure required to dissolve the thickener into the carbon dioxide is reduced by introducing segment containing fluorine and the solubility of the thickener in the carbon dioxide is improved. The hydrogen bond between the molecular of the thickener and the intertwined molecular chains increase the viscosity of the carbon dioxide effectively. The thickener is composed of ether groups as the spacers instead of ester groups, the $CO_2$-phillic groups and the association groups which are crosslinked by hydrogen bond, which effectively improves the thermal stability and hydrolysis stability of thickener molecules. The present invention can be applied in exploring oil and gas reservoir with active edge or bottom water.

A method for testing the viscosity of the thickener comprises the following steps: adding the supercritical carbon dioxide thickener with required mass fraction in a high temperature and high pressure closed system assembled with rheometer HAAKE™ MARS™ respectively; removing the air inside the closed system by a vacuum pump; guiding the corresponding supercritical carbon dioxide into the closed system through a sampling valve of the closed system; rotating the rotor in the closed system to blend the thickener and the carbon dioxide thoroughly and evenly; adjusting a system pressure and a system temperature to maintain the carbon dioxide in the closed system in a desirable state when the carbon dioxide goes into the meter; stirring the mixture and completing the mixing; turning on the rheometer; setting parameters; and measuring the viscosity of the mixture.

A method to evaluate the damage to the permeability of the dense matrix core and fracturing core by the thickened supercritical carbon dioxide gel using a core flooding system comprises the following steps: taking two rock cores from the tight reservoir; maintaining the core 1 unchanged to simulate the matrix core, cracking the core 2 into two halves to simulate the fracturing in the core; the core 1 or core 2 in the core clamper; applying vacuum saturation to the rock core in the clamper for 24 h; measuring the gas phase permeability $K_1$; injecting 0.1 PV gel into the core 1 or core 2; maintaining the gel in the cores for 48 h; injecting 0.2 PV natural gas into an outlet of the cores to simulate a flowback; forward measuring the gas phase permeability $K_2$; and calculating the damage to the permeability of the core 1 and core 2 by the supercritical carbon dioxide gel respectively with the equation $\eta=1-K_2/K_1$.

DETAILED DESCRIPTION OF THE PREFERRED EMBODIMENT

The present invention is illustrated by the below embodiments which are not a limitation of the present invention.

Embodiment 1

(1) Preparing the intermediate product (1) P-toluene perfluorooctyl ethylidene sulfonate, which further comprises following sub-steps: adding a perfluorooctyl alcohol and a P-toluenesulfonyl chloride in a three-neck flask, wherein a molar ratio of the perfluorooctyl alcohol and P-toluenesulfonyl chloride is 1:1.1; finally, adding a pyridine; wherein the system has reacted for 3 h under stirring thoroughly; maintaining a temperature at 0° C.; adding filter paper after a reaction process is over; carrying out ultrasonic dispersion for 1 h; removing unreacted residue P-toluenesulfonyl chloride; removing the filter paper; washing the system with 15% dilute hydrochloric acid for 3 times to remove the pyridine and collect a white solid; washing the solid with distilled water for 5 times; drying the solid by vacuum drying oven at 40° C. for 3 h to prepare an intermediate product (I) P-toluene perfluorooctyl ethylidene sulfonate; and (2) Preparing intermediate product (II) 1,3-bis(perfluorooctyl ethoxy) isopropyl-2-tertbutyl carbamate, which further comprises the following sub-steps: adding a 1,3-dihydroxy-propane-2-tert-butyl carbamate and the P-toluene perfluorooctyl ethylidene sulfonate in a three-neck flask, wherein a molar ratio of the (1,3-dihydroxy-propane-2-tert-butyl carbamate and P-toluene perfluorooctyl ethylidene sulfonate is 2.1:1; then adding potassium carbonate and N,N-dimethylformamide; wherein the system has been reacted for 4 h under stirring thoroughly at 40° C.; washing the reaction liquid with distilled water for five times after a reaction process is over; then carrying out the vacuum drying to collect an intermediate product (II) (1,3-bis(perfluorooctyl ethoxy) isopropyl-2-tertbutyl carbamate); and (3) Preparing a final product (III) 1,6-bis[1,3-bis(perfluorooctyl ethoxy) isopropyl-2-urea] hexane, which further comprises the following sub-steps: adding a mixture of methylene chloride and trifluoroacetic acid in a three-neck flask; a volume ratio of the methylene chloride and the three trifluoroacetic acid is 2:1; adding the intermediate product (II) 1,3-bis(perfluorooctyl ethoxy) isopropyl-2-tertbutyl carbamate to the mixture; maintaining a temperature at 45° C.; reacting for 2 h; adding the methylene chloride and extracting for 3 times to form an organic layer; drying the organic layer with a $Na_2SO_4$; adding HMDI, wherein a molar ratio of HMDI and 1,3-bis(perfluorooctyl ethoxy) isopropyl-2-tertbutyl carbamate is 1:2.05, reacting under a temperature of 50° C. for 2 h, washing a crude product with a mixture of ethyl acetate and benzene for 4 times; filtering and carrying out vacuum drying to collect a final product (III) 1,6-bis[1,3-bis(perfluorooctyl ethoxy) isopropyl-2-urea]hexane; and adding the supercritical carbon dioxide thickener 1,6-bis [1,3-bis(perfluorooctyl ethoxy) isopropyl-2-urea] hexane with a mass fraction of 0.5 wt %, 1.0 wt %, 1.5 wt %, 2.0 wt %, 2.5 wt %, 3.0 wt % in a high temperature and high pressure closed system assembled with supporting equipment, respectively; injecting the corresponding supercritical carbon dioxide into the closed system through a sampling valve; rotating the rotor and adjusting a system pressure and a system temperature; stirring a mixture of the thickener 1,6-bis[1,3-bis(perfluorooctyl ethoxy) isopropyl-2-urea] hexane and the corresponding supercritical carbon dioxide thoroughly to fully dissolve the supercritical carbon dioxide thickener; completing the mixing of two compounds and formatting the thickening supercritical carbon dioxide gel; setting a pressure at 28 MPa and a temperature at 60° C.; turning on a rheometer and maintaining a shear rate at 100 $s^{-1}$ during the experiment; measuring the viscosity of the mixture, wherein the viscosities are 2.35 mPa·s 4.12 mPa·s, 4.45 mPa·s 4.73 mPa·s, 5.01 mPa·s and 5.24 mPa·s, respectively, which are 58.8 times, 103.0 times, 111.3 times 118.5 times, 125.3 times and 131.0 times of the supercritical carbon dioxide without the thickener, respectively; evaluating the damage of the thickening supercritical carbon dioxide gel to the permeability of the tight matrix core and fracturing core by core flooding experiment, wherein the permeability damage rate of the tight matrix core and the fracturing core is 2.47% and 1.27%, respectively.

Embodiment 2

(1) Preparing the P-toluene perfluoropentyl ethylene sulfonate, which further comprises following sub-steps: adding a perfluoropentyl alcohol and a P-toluenesulfonyl chloride in a three-neck flask, wherein a molar ratio of the perfluoropentyl ethanol and P-toluenesulfonyl chloride is 1:1.2; finally, adding a pyridine; wherein the system has reacted for 3 h under stirring thoroughly; maintaining a temperature at 0° C.; adding filter paper after a reaction process is over, carrying out ultrasonic dispersion for 3 h; removing unreacted residue P-toluenesulfonyl chloride; removing the filter paper; washing the system with 15% dilute hydrochloric acid for 4 times to remove the pyridine and collect a white solid; washing the solid with distilled water for 5 times; drying the solid by vacuum drying oven at 40° C. for 3 hours to prepare an intermediate product (I) P-toluene perfluoropentyl ethylidene sulfonate; and (2) Preparing intermediate product (II) 1,3-bis(perfluoropentyl ethoxy) isopropyl-2-tertbutyl carbamate, which further comprises the following sub-steps: adding a 1,3-dihydroxy-propane-2-tert-butyl carbamate and the intermediate product (I) P-toluene perfluoropentyl ethylidene sulfonate in a three-neck flask, wherein a molar ratio of the (1,3-dihydroxy-propane-2-tert-butyl carbamate and intermediate product (I) P-toluene perfluoropentyl ethylidene sulfonate is 2.2:1; then adding potassium carbonate and N,N-dimethylformamide; wherein the system has been reacted for 4 h under stirring thoroughly at 40° C.; washing the reaction liquid with distilled water for 4 times after a reaction process is over; then carrying out the vacuum drying to collect an intermediate product (II) 1,3-bis(perfluoropentyl ethoxy) isopropyl-2-tertbutyl carbamate; and (3) Preparing a final product (III) 1,6-bis[1,3-bis(perfluoropentyl ethoxy) isopropyl-2-urea]hexane, which further comprises the following sub-steps: adding a mixture of methylene chloride and trifluoroacetic acid in a three-neck flask; a volume ratio of the methylene chloride and the three trifluoroacetic acid is 2:1; adding the intermediate product (II) 1,3-bis(perfluoropentyl ethoxy) isopropyl-2-tertbutyl carbamate to the mixture; maintaining a temperature at 45° C.; reacting for 2 h; adding the methylene chloride and extracting for 3 times to form an organic layer; drying the organic layer with a $Na_2SO_4$; adding HMDI, wherein a molar ratio of HMDI and 1,3-bis(perfluoropentyl ethoxy) isopropyl-2-tertbutyl carbamate is 1:2.10, reacting under a temperature of 50° C. for 2 h, washing a crude product with a mixture of ethyl acetate and benzene for 4 times; filtering and carrying out vacuum drying to collect a final product (III) 1,6-bis[1,3-bis(perfluoropentyl ethoxy) isopropyl-2-urea] hexane; and adding the supercritical carbon dioxide thickener 1,6-bis [1,3-bis(perfluoropentyl ethoxy) isopropyl-2-urea] hexane with a mass fraction of 0.5 wt %, 1.0 wt %, 1.5 wt %, 2.0 wt %, 2.5 wt %, 3.0 wt % in a high temperature and high pressure closed system assembled with supporting equipment, respectively; injecting the corresponding supercritical carbon dioxide into the closed system through a sampling valve; rotating the rotor and adjusting a system pressure and a system temperature; stirring a mixture of the thickener 1,6-bis[1,3-bis(perfluoropentyl ethoxy) isopropyl-2-urea] hexane and the corresponding supercritical carbon dioxide thoroughly to fully dissolve the supercritical carbon dioxide thickener; completing the mixing of two compounds and formatting the thickening supercritical carbon dioxide gel; setting a pressure at 28 MPa and a temperature at 60° C.; turning on a rheometer and maintaining a shear rate at 100 $s^{-1}$ during the experiment; measuring the viscosity of the mixture, wherein the viscosities are 1.87 mPa·s 3.35 mPa·s, 3.52 mPa·s 3.76 mPa·s, 3.98 mPa·s and 4.13 mPa·s, which are 46.8 times, 83.8 times, 88.0 times 94.0 times, 99.5 times and 103.3 times of the supercritical carbon dioxide without the thickener, respectively; evaluating the damage of the thickening supercritical carbon dioxide gel to the permeability of the tight matrix core and fracturing core by core flooding experiment, wherein the permeability damage rate of the tight matrix core and the fracturing core is 3.36% and 1.73%, respectively.

Embodiment 3

(1) Preparing the P-toluene perfluoroheptyl ethylene sulfonate, which further comprises following sub-steps: adding a perfluoroheptyl alcohol and a P-toluenesulfonyl chloride in a three-neck flask, wherein a molar ratio of the perfluoroheptyl ethanol and P-toluenesulfonyl chloride is 1:1.15; finally, adding a pyridine; wherein the system has reacted for 3 h under stirring thoroughly; maintaining a temperature at 10° C.; adding filter paper after a reaction process is over; carrying out ultrasonic dispersion for 1 h; removing unreacted residue P-toluenesulfonyl chloride; removing the filter paper washing the system with 15% dilute hydrochloric acid for 5 times to remove the pyridine and collect a white solid; washing the solid with distilled water for 5 times; drying the solid by vacuum drying oven at 40° C. for 3 h to prepare an intermediate product (I) P-toluene perfluoroheptyl ethylidene sulfonate; and (2) Preparing intermediate product (II) 1,3-bis(perfluoroheptyl ethoxy) isopropyl-2-tertbutyl carbamate, which further comprises the following sub-steps: adding a 1,3-dihydroxy-propane-2-tert-butyl carbamate and the intermediate product (I) P-toluene perfluoroheptyl ethylidene sulfonate in a three-neck flask, wherein a molar ratio of the (1,3-dihydroxy-propane-2-tert-butyl carbamate and intermediate product (I) P-toluene perfluoroheptyl ethylidene sulfonate is 2.15:1; then adding potassium carbonate and N,N-dimethylformamide; wherein the system has been reacted for 4 h under stirring thoroughly at 40° C.; washing the reaction liquid with distilled water for 4 times after a reaction process is over; then carrying out the vacuum drying to collect an intermediate product (II) 1,3-bis(perfluoroheptyl ethoxy) isopropyl-2-tertbutyl carbamate; and (3) Preparing a final product (III) 1,6-bis[1,3-bis(perfluoroheptyl ethoxy) isopropyl-2-urea]hexane, which further comprises the following sub-steps: adding a mixture of methylene chloride and trifluoroacetic acid in a three-neck flask; a volume ratio of the methylene chloride and the three trifluoroacetic acid is 2:1; adding the intermediate product (II) 1,3-bis(perfluoroheptyl ethoxy) isopropyl-2-tertbutyl carbamate to the mixture; maintaining a temperature at 45° C.; reacting for 2 h; adding to the methylene chloride and extracting for 3 times to form an organic layer; drying the organic layer with a $Na_2SO_4$; adding HMDI wherein a molar ratio of HMDI and 1,3-bis(perfluoroheptyl ethoxy) isopropyl-2-tertbutyl carbamate is 1:2.10, reacting under a temperature of 50° C. for 2 h, washing a crude product with a mixture of ethyl acetate and benzene for 5 times; filtering and carrying out vacuum drying to collect a final product (III) 1,6-bis[1,3-bis(perfluoroheptyl ethoxy) isopropyl-2-urea]hexane; and adding the supercritical carbon dioxide thickener 1,6-bis[1,3-bis(perfluoroheptyl ethoxy) isopropyl-2-urea]hexane with a mass fraction of 0.5 wt %, 1.0 wt %, 1.5 wt %, 2.0 wt %, 2.5 wt %, 3.0 wt % in a high temperature and high pressure closed system assembled with supporting equipment, respectively; injecting the corresponding supercritical carbon dioxide into the closed system through a sampling valve; rotating the rotor and adjusting a system pressure and a system temperature; stirring a mixture of the thickener 1,6-bis[1,3-bis(perfluoroheptyl ethoxy) isopropyl-2-urea] hexane and the corresponding supercritical carbon dioxide thoroughly to fully dissolve the supercritical carbon dioxide thickener; completing the mixing of two compounds and formatting the thickening supercritical carbon dioxide gel; setting a pressure at 28 MPa and a temperature at 60° C.; turning on a rheometer and maintaining a shear rate at 100 $s^{-1}$ during the experiment; measuring the viscosity of the mixture, wherein the viscosities are 1.99 mPa·s 3.46 mPa·s, 3.63 mPa·s 3.84 mPa·s, 4.12 mPa·s and 4.48 mPa·s, which are 49.8 times, 86.5 times, 90.8 times, 96.0 times, 103.0 times and 112.0 times of the supercritical carbon dioxide without the thickener, respectively evaluating the damage of the thickening supercritical carbon dioxide gel to the permeability of the tight matrix core and fracturing core by core flooding experiment, wherein the permeability damage rate of the tight matrix core and the fracturing core is 3.67% and 1.58%, respectively.

Embodiment 4

(1) Preparing the P-toluene perfluorohexyl ethylene sulfonate, which further comprises following sub-steps: adding perfluorohexyl alcohol and a P-toluenesulfonyl chloride in a three-neck flask, wherein a molar ratio of the perfluorohexyl ethanol and P-toluenesulfonyl chloride is 1:1.12; finally, adding a pyridine; wherein the system has reacted for 3 h under stirring thoroughly; maintaining a temperature at 10° C.; adding filter paper after a reaction process is over; carrying out ultrasonic dispersion for 1 hour; removing unreacted residue P-toluenesulfonyl chloride; removing the filter paper; washing the system with 15% dilute hydrochloric acid for 5 times to remove the pyridine and collect a white solid; washing the solid with distilled water for five times; drying the solid by vacuum drying oven at 40° C. for 3 h to prepare an intermediate product (I) P-toluene perfluorohexyl ethylidene sulfonate; and (2) Preparing intermediate product (II) 1,3-bis(perfluorohexyl ethoxy) isopropyl-2-tertbutyl carbamate, which further comprises the following sub-steps: adding a 1,3-dihydroxy-propane-2-tert-butyl carbamate and the intermediate product (I) P-toluene perfluorohexyl ethylidene sulfonate in a three-neck flask, wherein a molar ratio of the (1,3-dihydroxy-propane-2-tert-butyl carbamate and intermediate product (I) P-toluene perfluorohexyl ethylidene sulfonate is 2.10:1; then adding potassium carbonate and N,N-dimethylformamide; wherein the system has been reacted for 4 h under stirring thoroughly at 40° C.; washing the reaction liquid with distilled water for 4 times after a reaction process is over; then carrying out the vacuum drying to collect an intermediate product (II) 1,3-bis(perfluorohexyl ethoxy) isopropyl-2-tertbutyl carbamate; and (3) Preparing a final product (III) 1,6-bis[1,3-bis(perfluorohexyl ethoxy) isopropyl-2-urea]hexane, which further comprises the following sub-steps: adding a mixture of methylene chloride and trifluoroacetic acid in a three-neck flask; a volume ratio of the methylene chloride and the three trifluoroacetic acid is 2:1; adding the intermediate product (II) 1,3-bis(perfluorohexyl ethoxy) isopropyl-2-tertbutyl carbamate to the mixture; maintaining a temperature at 45° C.; reacting for 2 h; adding the methylene chloride and extracting for 3 times to form an organic layer drying the organic layer with a $Na_2SO_4$; adding HMDI, wherein a molar ratio of HMDI and 1,3-bis(perfluorohexyl ethoxy) isopropyl-2-tertbutyl carbamate is 1:2.05, reacting under a temperature of 50° C. for 2 h, washing a crude product with a mixture of ethyl acetate and benzene for 5 times; filtering and carrying out vacuum drying to collect a final product (III) 1,6-bis[1,3-bis(perfluorohexyl ethoxy) isopropyl-2-urea] hexane; and adding the supercritical carbon dioxide thickener 1,6-bis[1,3-bis(perfluorohexyl ethoxy) isopropyl-2-urea]hexane with a mass fraction of 0.5 wt %, 1.0 wt %, 1.5 wt %, 2.0 wt %, 2.5 wt %, 3.0 wt % in a high temperature and high pressure closed system assembled with supporting equipment, respectively; injecting the corresponding supercritical carbon dioxide into the closed system through a sampling valve; rotating the rotor and adjusting a system pressure and a system temperature; stirring a mixture of the thickener 1,6-bis[1,3-bis(perfluorohexyl ethoxy) isopropyl-2-urea] hexane and the corresponding supercritical carbon dioxide thoroughly to fully dissolve the supercritical carbon dioxide thickener; completing the mixing of two compounds and formatting the thickening supercritical carbon dioxide gel; setting a pressure at 28 MPa and a temperature at 60° C.; turning on a rheometer and maintaining a shear rate at 100 $s^{-1}$ during the experiment; measuring the viscosity of the mixture, wherein the viscosities are 1.90 mPa·s 3.42 mPa·s, 3.56 mPa·s 3.79 mPa·s, 4.06 mPa·s and 4.33 mPa·s, which are 47.5 times, 85.5 times, 89.0 times, 94.8 times, 101.5 times and 108.3 times of the supercritical carbon dioxide without the thickener, respectively; evaluating the damage of the thickening supercritical carbon dioxide gel to the permeability of the tight matrix core and fracturing core by core flooding experiment, wherein the permeability damage rate of the tight matrix core and the fracturing core is 3.85% and 1.36%, respectively.

Embodiment 5

(1) Preparing the P-toluene perfluorodecyl ethylene sulfonate, which further comprises following sub-steps: adding a perfluorodecyl alcohol and a P-toluenesulfonyl chloride in a three-neck flask, wherein a molar ratio of the perfluorodecyl ethanol and P-toluenesulfonyl chloride is 1:1.12; finally, adding a pyridine; wherein the system has reacted for 3 h under stirring thoroughly; maintaining a temperature at 10° C.; adding filter paper after a reaction process is over, carrying out ultrasonic dispersion for 1 h; removing unreacted residue P-toluenesulfonyl chloride; removing the filter paper; washing the system with 15% dilute hydrochloric acid for 5 times to remove the pyridine and collect a white solid; washing the solid with distilled water for 5 times; drying the solid by vacuum drying oven at 40° C. for 3 h to prepare an intermediate product (I) P-toluene perfluorodecyl ethylidene sulfonate; and (2) Preparing intermediate product (II) 1,3-bis(perfluorodecyl ethoxy) isopropyl-2-tertbutyl carbamate, which further comprises the following sub-steps: adding a 1,3-dihydroxy-propane-2-tert-butyl carbamate and the intermediate product (I) P-toluene perfluorodecyl ethylidene sulfonate in a three-neck flask, wherein a molar ratio of the (1,3-dihydroxy-propane-2-tert-butyl carbamate and intermediate product (1) P-toluene perfluorodecyl ethylidene sulfonate is 2.10:1; then adding potassium carbonate and N,N-dimethylformamide; wherein the system has been reacted for 4 h under stirring thoroughly at 40° C.; washing the reaction liquid with distilled water for 4 times after a reaction process is over; then carrying out the vacuum drying to collect an intermediate product (II) 1,3-bis(perfluorodecyl ethoxy) isopropyl-2-tertbutyl carbamate; and (3) Preparing a final product (III) 1,6-bis[1,3-bis(perfluorodecyl ethoxy) isopropyl-2-urea] hexane, which further comprises the following sub-steps: adding a mixture of methylene chloride and trifluoroacetic acid in a three-neck flask; a volume ratio of the methylene chloride and the three trifluoroacetic acid is 2:1; adding the intermediate product (II) 1,3-bis(perfluorodecyl ethoxy) isopropyl-2-tertbutyl carbamate to the mixture; maintaining a temperature at 45° C.; reacting for 2 h; adding the methylene chloride and extracting for 3 times to form an organic layer, drying the organic layer with a $Na_2SO_4$; adding HMDI, wherein a molar ratio of HMDI and 1,3-bis(perfluorodecyl ethoxy) isopropyl-2-tertbutyl carbamate is 1:2.05, reacting under a temperature of 50° C. for 2 h, washing a crude product with a mixture of ethyl acetate and benzene for 5 times; filtering and carrying out vacuum drying to collect a final product (III) 1,6-bis[1,3-bis(perfluorodecyl ethoxy) isopropyl-2-urea] hexane; and adding the supercritical carbon dioxide thickener 1,6-bis[1,3-bis(perfluorodecyl ethoxy) isopropyl-2-urea] hexane with a mass fraction of 0.5 wt %, 1.0 wt %, 1.5 wt %, 2.0 wt %, 2.5 wt %, 3.0 wt % in a high temperature and high pressure closed system assembled with supporting equipment, respectively; injecting the corresponding supercritical carbon dioxide into the closed system through a sampling valve; rotating the rotor and adjusting a system pressure and a system temperature; stirring a mixture of the thickener 1,6-bis[1,3-bis(perfluorodecyl ethoxy) isopropyl-2-urea] hexane and the corresponding supercritical carbon dioxide thoroughly to fully dissolve the supercritical carbon dioxide thickener; completing the mixing of two compounds and formatting the thickening supercritical carbon dioxide gel; setting a pressure at 28 MPa and a temperature at 60° C.; turning on a rheometer and maintaining a shear rate at 100 $s^{-1}$ during the experiment; measuring the viscosity of the mixture, wherein the viscosities are 1.55 mPa·s 2.76 mPa·s, 3.22 mPa·s 3.43 mPa·s, 3.61 mPa·s and 3.78 mPa·s, which are 38.8 times, 69.0 times, 80.5 times, 85.8 times, 90.3 times and 94.5 times of the supercritical carbon dioxide without the thickener, respectively; evaluating the damage of the thickening supercritical carbon dioxide gel to the permeability of the tight matrix core and fracturing core by core flooding experiment, wherein the permeability damage rate of the tight matrix core and the fracturing core is 2.23% and 1.45%, respectively.

What is claimed is:

1. A method for preparing a supercritical carbon dioxide thickener for a tight oil and gas reservoir, comprising following steps:
   (1) preparing P-toluene perfluoroalkyl ethylenesulfonates (TFES), which further comprises following sub-steps: after adding a perfluoroalkyl alcohol and a P-toluenesulfonyl chloride in a three-neck flask, wherein a molar ratio of the perfluoroalkyl alcohol and the P-toluenesulfonyl chloride is 1:1.1-1.2, and adding a pyridine; forming a system; wherein the system has reacted for 3 h under stirring thoroughly; maintaining a temperature at 0-20° C.; adding filter paper and carrying out ultrasonic dispersion for 1 h after a reaction is over; after removing unreacted residue P-toluenesulfonyl chloride and the filter paper; forming a system; washing the system with 15% dilute hydrochloric acid many times to remove the pyridine and collect a white solid; washing the white solid with distilled water for multiple times, drying the white solid by a vacuum drying oven at 40° C. for 3 h to prepare an intermediate product (I) TFES;
   (2) preparing intermediate product (II) (1,3-bis(perfluoroalkyl ethoxy) isopropyl-2-tertbutyl carbamate) (PFEIT), which further comprises the following sub-steps: adding a 1,3-dihydroxy-propane-2-tert-butyl carbamate and the intermediate product (I) TFES in a three-neck flask, wherein a molar ratio of the 1,3-dihydroxy-propane-2-tert-butyl carbamate and the TFES is 2.1-2.2:1; then adding potassium carbonate and N,N-dimethylformamide; forming a system; wherein the system has been reacted for 4 h under stirring thoroughly at 40° C.; washing a reaction liquid with distilled water repeatedly after a reaction process is over; then carrying out vacuum drying to collect an intermediate product (II) PFEIT; and
   (3) preparing a final product (III) 1,6-bis[1,3-bis(perfluoroalkyl ethoxy) isopropyl-2-urea] hexane (PFEIUH), which further comprises the following sub-steps: adding a mixture of methylene chloride and trifluoroacetic acid in a three-neck flask; wherein a volume ratio of the methylene chloride and the three trifluoroacetic acid is 2:1; adding the intermediate product (III) PFEIT to the mixture; maintaining a temperature at 45° C.; reacting for 2 h; adding the methylene chloride for extracting for 3 times to form an organic layer; drying the organic layer with a $Na_2SO_4$; adding 1,6-hexamethylene diisocyanate (HMDI), wherein a molar ratio of the HMDI and the PFEIT is 1:2.05-2.10, reacting under a temperature of 50° C. for 2 h, washing a crude product with a mixture of ethyl acetate and benzene for multiple times; filtering and carrying out vacuum drying to collect a final product (III) PFEIUH, wherein a perfluoro alkyl is one from these groups $C_5F_{11}$, $C_6F_{13}$, $C_7F_{15}$, $C_8F_{17}$, $C_9F_{19}$, $C_{10}F_{21}$.

* * * * *